(12) United States Patent
Kuske et al.

(10) Patent No.: US 7,021,466 B2
(45) Date of Patent: Apr. 4, 2006

(54) FLEXIBLE PACKAGING BAG WITH VISUAL DISPLAY FEATURE

(75) Inventors: Marci Elizabeth Kuske, Appleton, WI (US); Anne Louise Miller, Appleton, WI (US); Leonard Michael Kaczmarzyk, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/299,279

(22) Filed: Nov. 19, 2002

(65) Prior Publication Data

US 2003/0070955 A1   Apr. 17, 2003

Related U.S. Application Data

(63) Continuation of application No. 09/802,750, filed on Mar. 8, 2001, now Pat. No. 6,491,165, which is a continuation of application No. 08/671,232, filed on Jun. 27, 1996, now Pat. No. 6,318,555.

(51) Int. Cl.
*B65D 33/00* (2006.01)

(52) U.S. Cl. ............... 206/494; 206/459.5; 383/66; 383/106; 383/207

(58) Field of Classification Search ............ 206/459.5, 206/494, 457, 526, 769, 770, 776, 778, 781, 206/499, 782; 383/94, 106; 604/358, 358.1
See application file for complete search history.

(56) References Cited

U.S. PATENT DOCUMENTS

| 1,977,687 | A | 10/1934 | Medoff |
|---|---|---|---|
| 2,022,906 | A | 12/1935 | Weeks |
| 2,025,969 | A | 12/1935 | Broeren |
| 2,649,807 | A | 8/1953 | Ritter |
| 2,773,589 | A | 12/1956 | Hennessey |
| 3,051,584 | A | 8/1962 | Tindall |
| 3,149,431 | A | 9/1964 | Blish |
| 3,481,454 | A | 12/1969 | King |
| 3,580,466 | A | 5/1971 | Thelen et al. |

(Continued)

FOREIGN PATENT DOCUMENTS

BE   524 328   12/1953

(Continued)

OTHER PUBLICATIONS

Derwent World Patent Abstract CH 598069, Apr. 28, 1978.

(Continued)

*Primary Examiner*—Luan K. Bui
(74) *Attorney, Agent, or Firm*—Brinks Hofer Gilson & Lione

(57) ABSTRACT

A packaging bag for containing a plurality of disposable absorbent articles includes a generally polyhedral enclosure having an interior space, a pair of side walls, a pair of end walls, a top wall, and a bottom wall. A plurality of disposable absorbent articles contained in the interior space, with each one of the articles being adapted to be worn by a user and including a front panel and a back panel. A first graphic is provided on the front panel of each the absorbent article, and a second graphic is provided on the back panel of each the absorbent article. A first and a second of the walls include an at least substantially clear portion, with the plurality of disposable absorbent articles being folded and positioned in the enclosure such that at least a portion of the first graphic is visually perceivable through the first of the walls and at least a portion of the second graphic is visually perceivable through the second of the walls.

27 Claims, 7 Drawing Sheets

U.S. PATENT DOCUMENTS

| | | | |
|---|---|---|---|
| 3,872,966 A | 3/1975 | Gordon et al. |
| 4,252,269 A | 2/1981 | Peppiatt |
| 4,381,058 A | 4/1983 | Chaussadas et al. |
| 4,460,741 A | 7/1984 | Dufour et al. |
| 4,570,796 A | 2/1986 | Groom |
| 4,691,368 A | 9/1987 | Roessiger |
| 4,696,050 A | 9/1987 | Sengewald |
| 4,700,841 A | 10/1987 | Padgett, Jr. et al. |
| 4,713,839 A | 12/1987 | Peppiatt |
| 4,715,511 A | 12/1987 | Bohlen |
| 4,738,546 A | 4/1988 | Sengewald |
| 4,750,616 A | 6/1988 | Bridges |
| 4,846,587 A | 7/1989 | Hull |
| 4,854,733 A | 8/1989 | Schwinn |
| 4,857,037 A | 8/1989 | Schwinn |
| 4,867,575 A | 9/1989 | Wood |
| 4,874,255 A | 10/1989 | Ball et al. |
| 4,877,335 A | 10/1989 | Barnard |
| 4,877,337 A | 10/1989 | Wood |
| 4,913,693 A | 4/1990 | Ball et al. |
| 4,934,535 A | 6/1990 | Muckenfuhs et al. |
| 4,940,464 A | 7/1990 | Van Gompel et al. |
| 4,966,286 A | 10/1990 | Muckenfuhs |
| 4,982,845 A | 1/1991 | Prascak et al. |
| 4,989,993 A | 2/1991 | Barnard |
| 5,022,216 A | 6/1991 | Muckenfuhs et al. |
| 5,033,868 A | 7/1991 | Peppiatt |
| 5,036,978 A | 8/1991 | Frank et al. |
| 5,046,272 A | 9/1991 | Vogt et al. |
| 5,048,687 A | 9/1991 | Suzuki et al. |
| 5,050,742 A | 9/1991 | Muckenfuhs |
| 5,054,619 A | 10/1991 | Muckenfuhs |
| 5,065,868 A | 11/1991 | Cirnelissen et al. |
| 5,067,612 A | 11/1991 | Tsuchiya et al. |
| 5,080,497 A | 1/1992 | Peppiatt |
| 5,104,116 A | 4/1992 | Pohjola |
| 5,121,995 A | 6/1992 | Newman et al. |
| 5,150,561 A | 9/1992 | Muckenfuhs |
| 5,158,499 A | 10/1992 | Guckenberger |
| 5,163,558 A | 11/1992 | Palumbo et al. |
| 5,174,657 A | 12/1992 | Peppiat |
| 5,219,229 A | 6/1993 | Sengewald |
| 5,224,405 A | 7/1993 | Pohjola |
| 5,282,687 A | 2/1994 | Yee |
| 5,361,905 A | 11/1994 | McQueeny et al. |
| 5,377,837 A | 1/1995 | Roussel |
| 5,380,094 A | 1/1995 | Schmidt et al. |
| 5,427,245 A | 6/1995 | Roussel |
| 5,458,590 A | 10/1995 | Schleinz et al. |
| 5,575,782 A | 11/1996 | Hasse et al. |
| 5,967,665 A | 10/1999 | MacDonald et al. |
| 6,318,555 B1 | 11/2001 | Kuske et al. |

FOREIGN PATENT DOCUMENTS

| | | |
|---|---|---|
| CA | 1 240 651 | 8/1988 |
| CA | 2012845 | 10/1990 |
| CA | 1277288 | 12/1990 |
| CA | 2019189 | 12/1990 |
| CA | 2019715 | 12/1990 |
| CA | 1282379 | 4/1991 |
| CA | 2068316 | 6/1991 |
| CA | 1286643 | 7/1991 |
| CA | 1291459 | 10/1991 |
| CA | 2014080 | 10/1991 |
| CA | 2043687 | 12/1991 |
| CA | 2046458 | 1/1992 |
| CA | 2047819 | 2/1992 |
| CA | 2032252 | 6/1992 |
| CA | 1308391 | 10/1992 |
| CA | 2079965 | 8/1993 |
| CA | 1322340 | 9/1993 |
| CA | 2084150 | 2/1994 |
| CA | 2124128 | 3/1995 |
| CA | 2095021 | 9/1995 |
| CN | CH 598069 | 4/1978 |
| DE | 31 02 192 A1 | 1/1981 |
| DE | 36 22 968 A1 | 7/1986 |
| DE | 36 44 618 A1 | 12/1986 |
| DE | 36 44 620 A1 | 12/1986 |
| DE | 37 04 846 A1 | 2/1987 |
| EP | 0 356 319 A1 | 2/1990 |
| EP | 0 585 653 A1 | 3/1994 |
| EP | 0 425 008 B1 | 12/1994 |
| FR | 1441107 | 12/1966 |
| FR | 2476464 | 8/1981 |
| FR | 2679531 | 1/1993 |
| GB | 2 003 838 A | 3/1979 |
| GB | 2 113 651 A | 8/1983 |
| JP | 48-96085 | 11/1973 |
| JP | 59-78279 | 5/1984 |
| JP | 59 96155 | 6/1984 |
| JP | 63-67478 | 6/1988 |
| JP | 01 009177 | 1/1989 |
| JP | 64 9177 | 1/1989 |
| JP | 3-669 | 1/1991 |
| JP | 3-212339 | 9/1991 |
| JP | 4 72123 | 3/1992 |
| JP | 5-503059 | 5/1993 |
| JP | 3011440 | 3/1995 |
| WO | WO 91/08962 | 6/1991 |
| WO | WO 92/18396 | 10/1992 |
| WO | WO 94/20378 | 9/1994 |
| WO | WO 94/22739 | 10/1994 |

OTHER PUBLICATIONS

Patent Cooperation Treaty Search Report from the International Search Authority, International Application No. PCT/US 97/10721 dated Sep. 26, 1997.

Notification of Reason for Rejection to Mr. M. Nakamura et al. from H. Ishida, re Patent Application No. 10-503374 dated Jul. 8, 2004, one page.

(Translation) Certified Copy of Decision of Rejection, dated Nov. 26, 2004, Applicant: Kimberly-Clark Worldwide, Inc., Patent Application No. 10-503374, 2 pages.

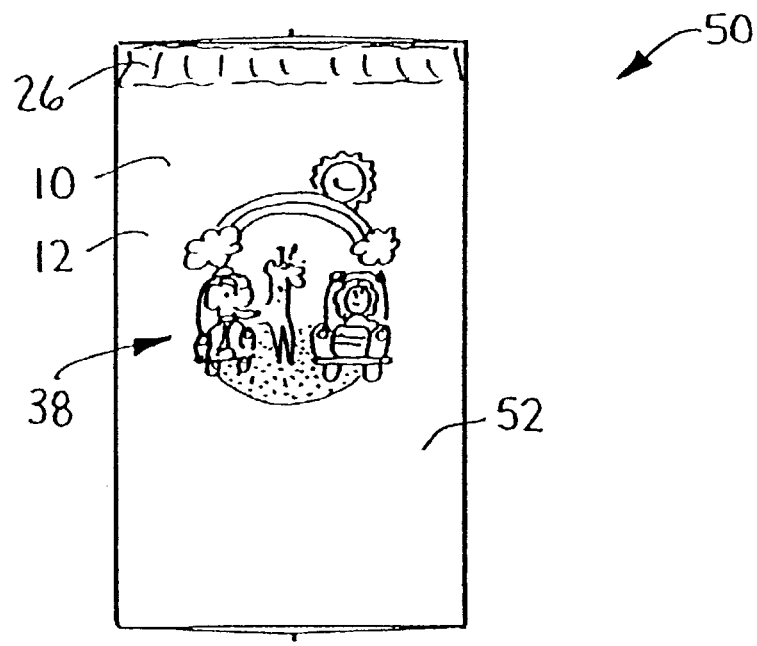
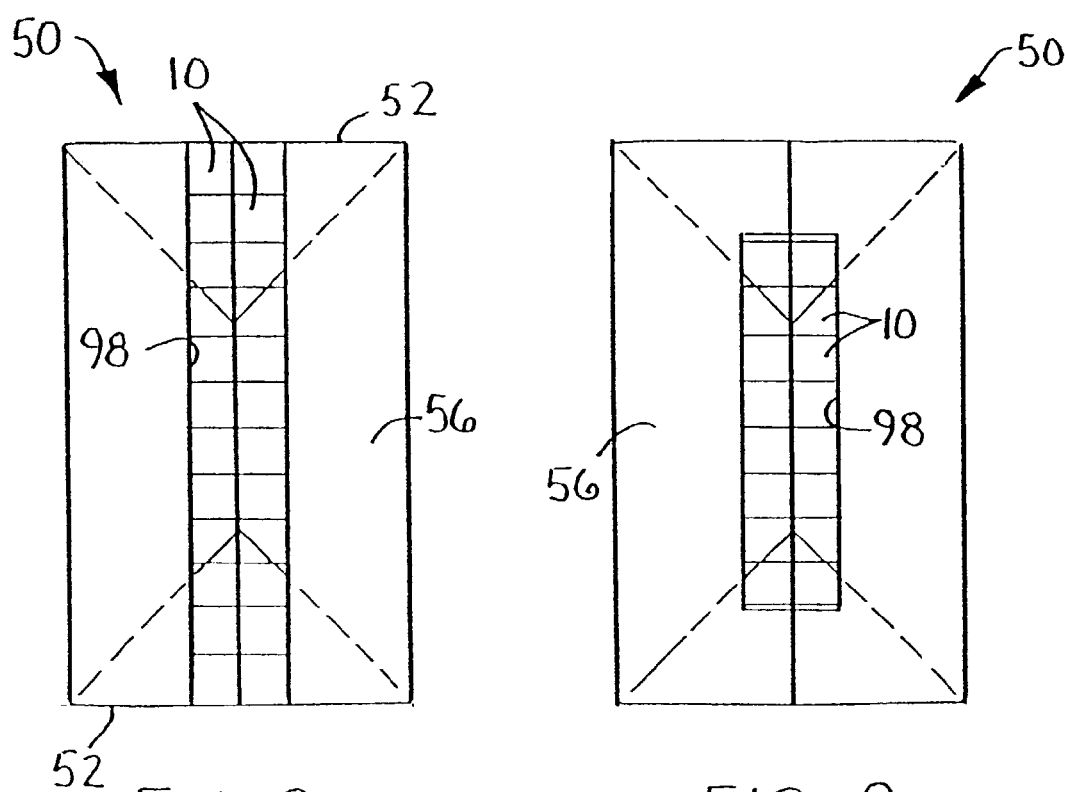

FLEXIBLE PACKAGING BAG WITH VISUAL DISPLAY FEATURE

This application is a continuation of U.S. patent application Ser. No. 09/802,750, entitled "Flexible Packaging Bag With Visual Display Feature," filed Mar. 8, 2001, now U.S. Pat. No. 6,491,165, which is a continuation of U.S. application Ser. No. 08/671,232, entitled "Flexible Packaging Bag With Visual Display Feature," filed Jun. 27, 1996, now U.S. Pat. No. 6,318,555.

BACKGROUND OF THE INVENTION

The present invention relates to flexible packaging bags for containing and dispensing articles. More particularly, the present invention relates to a flexible packaging bag having a visual display feature permitting selected portions of the contained articles to be visually perceivable.

Packaging bags composed of flexible polymer materials have been used for packaging various types of products, such as infant diapers, training pants, feminine care products, and adult incontinence garments. These bags allow packaging of the articles to create a carton-like look and a configuration facilitating transportation and display on retail shelves. The bags may include handles to facilitate the carrying of the bags, and can include mechanisms for providing an access opening in the package.

In order to inform the consumer of the contents of a particular bag, the material of which the bag is made is printed with written information, illustrations, or the like appropriate for the particular articles. Generally, the material of which the bag is made will be printed with a background color, and upon this background color will be further printed an illustration of the contained articles and terminology describing the article, its use, the manufacturer, or the like.

One of the problems with the current printing of these bags is that they may not be truly representative of the actual product contained therein. This can have the undesirable effect of decreasing the credibility of the consumer in the product's structure, and thus its performance.

SUMMARY OF THE INVENTION

In response to the discussed difficulties and problems encountered in the prior art, a flexible packaging bag having a visual display feature has been discovered.

In one form of the invention there is provided a packaging bag having a pair of side walls, a pair of end walls, a top wall, and a bottom wall; all of the walls defining an interior space. A stack of articles are contained in the interior space, and each of the articles includes a front panel and a back panel with a graphic on one of the panels. One of the walls has a window having a periphery substantially framing at least a portion of the graphic.

In another form of the present invention there is provided a packaging bag having a pair of side walls, a pair of end walls, a top wall, and a bottom wall, all of which define an interior space. A stack of articles are contained in the interior space. A window substantially wraps around four of the walls, and at least a segment of a component of the articles is visually perceivable through the window.

In yet another form of the present invention there is provided a packaging bag having a plurality of walls forming a polyhedral enclosure having an interior space. A stack of articles is contained in the interior space, and each of the articles has a component associated therewith. At least a portion of one of the walls is at least substantially clear, and the stack of articles are positioned in the interior space so that at least a segment of the component is visually perceivable through the substantially clear portion.

In still yet another form of the invention there is provided a packaging bag having a substantially transparent enclosure defined by a plurality of sides forming an interior space. A stack of articles are contained in the interior space, and each article has a front panel and a back panel. At least one of the panels of each article includes a graphic thereon. A mechanism is provided for accessing the interior space for dispensing the articles.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings wherein:

FIG. 7 illustrates a front view of a fourth bag of the present invention;

FIG. 8 illustrates a top view of a fifth bag of the present invention;

FIG. 9 illustrates a top view of a sixth bag of the present invention;

DESCRIPTION OF A PREFERRED EMBODIMENT

Figure 1:
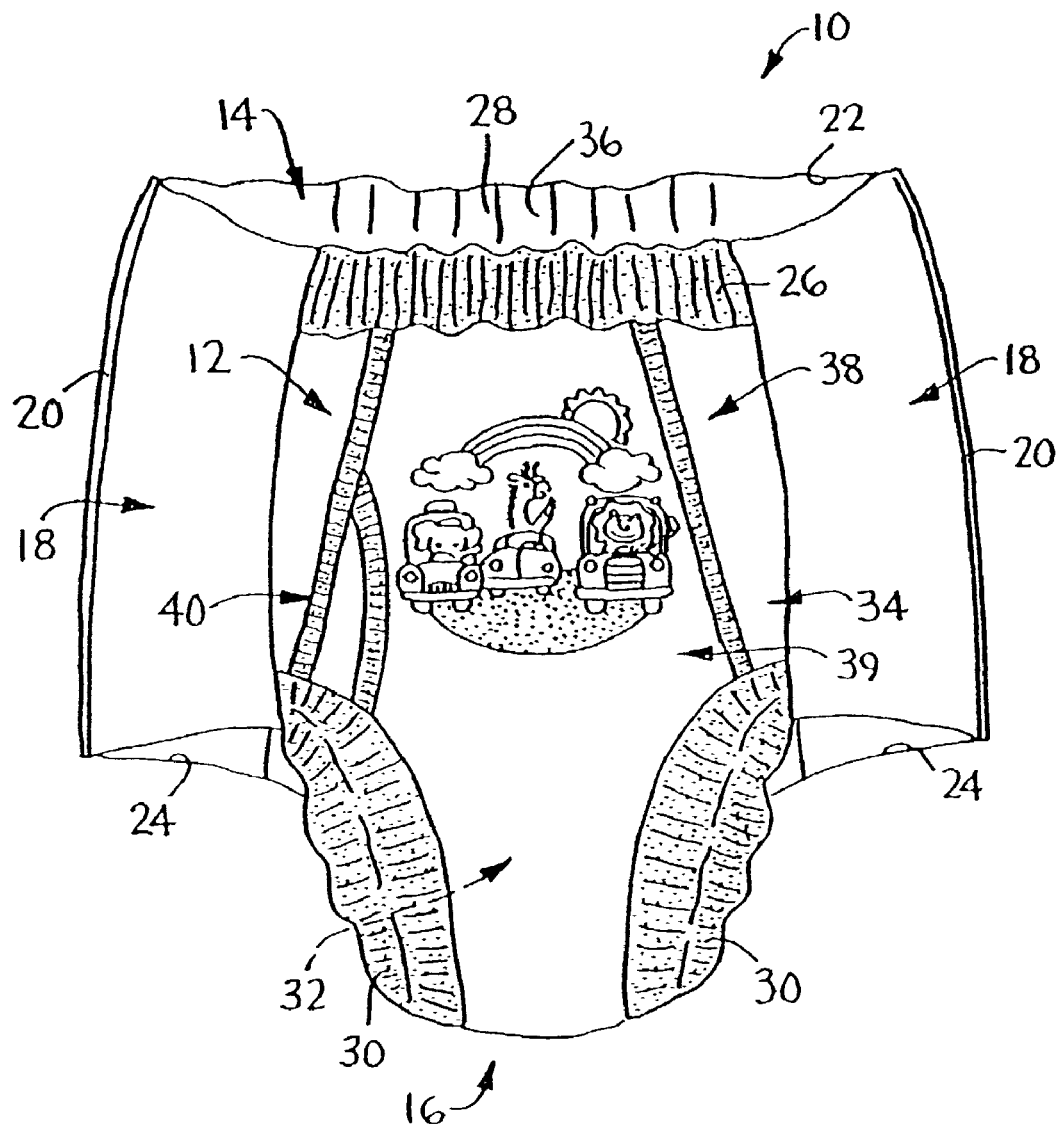
FIG. 1 illustrates a front view of one article having a graphic thereon.
Figure 2:
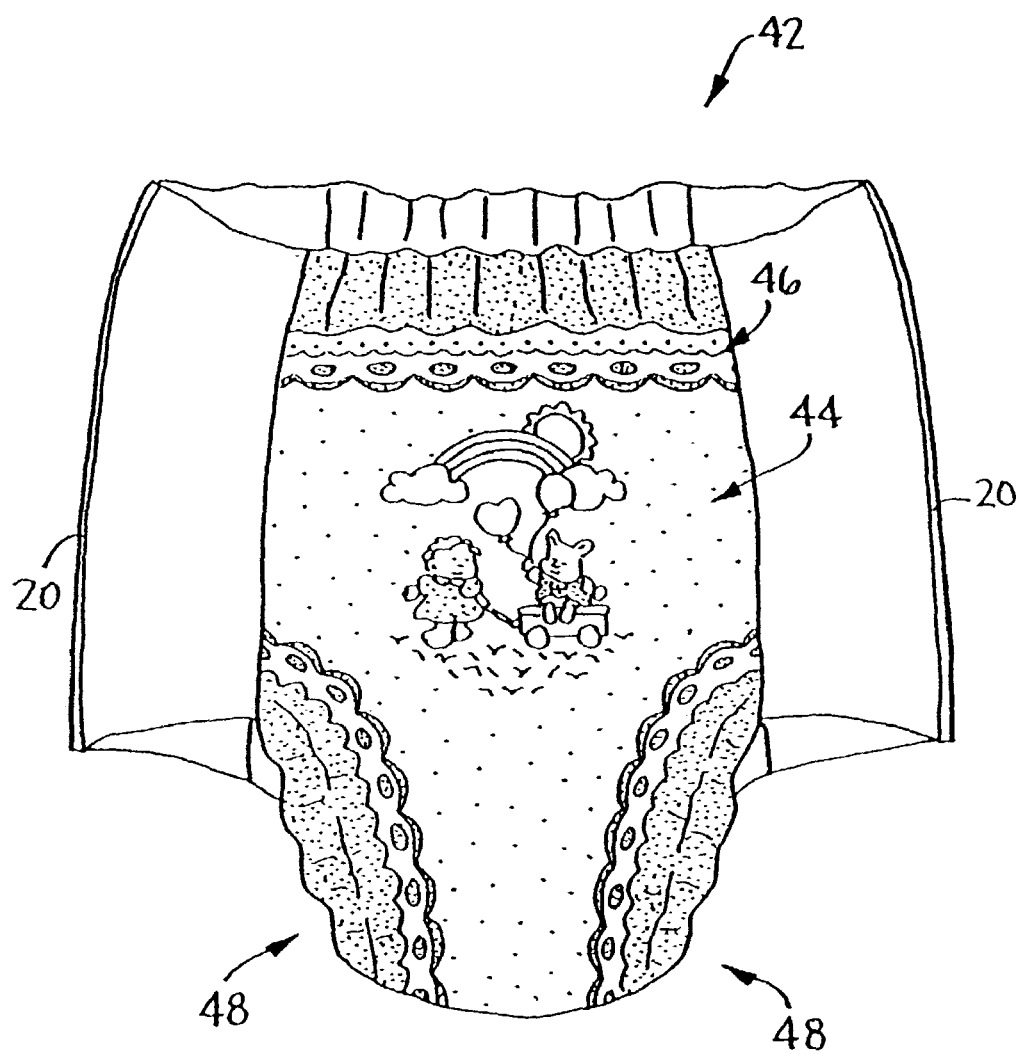
FIG. 2 illustrates a front view of another article having a graphic thereon.

FIGS. 1 and 2 illustrate a child's disposable absorbent training pant, in which the term "disposable" means that the training pant is designed to be used until soiled and then discarded, rather than being washed and being reused again. Examples of other suitable disposable absorbent articles that can be used with the flexible packaging bag of the present invention include, but are not limited to, disposable absorbent pants, diapers, feminine care products, incontinence products, disposable apparel, or the like. Hereafter, when used with reference to, by way of example, a disposable training pant, the term "component" can refer, but is not limited, to all or a segment of a designated selected region, such as edges, corners, sides or the like; structural members such as elastic strips, absorbent pads, elastic layers or panels, layers of material, or the like; or a graphic. The term "graphic" can refer, but is not limited, to an image, design, pattern, symbology, indicia, or the like.

A disposable absorbent article, such as the training pant illustrated in FIG. 1 or 2, can have multiple appearance-related and/or function-related components. Examples of components that are appearance-related include, but are not limited to, graphics; the highlighting or emphasizing of leg and waist openings in order to make product shaping more evident or visible; the highlighting or emphasizing of areas of the article to simulate functional components such as elastic leg bands, elastic waistbands, simulated "fly openings" for boys, or ruffles for girls; the highlighting of areas of the product to change the appearance of the size of the product; selectively positioned wetness indicators; back labels or front labels; and selectively positioned written instructions at a desired location on the article.

Examples of functional components include, but are not limited to, waist elastics, leg elastics, areas of breathability, fluid repellent areas, fluid wettable areas, adhesives, coatings, encapsulated inks, chemically-sensitive materials, environmentally-sensitive materials, heat-sensitive materials, moisture-sensitive materials, perfumes, odor control agents, inks, fasteners, fluid storage areas, textured or embossed areas, or the like.

Referring now to FIG. 1, there is illustrated a child's disposable training pant 10 generally comprising a front panel 12, a back panel 14, a crotch panel 16 interconnecting front and back panels 12, 14, and a pair of elastic side panels 18. Each elastic side panel 18 is formed from two separate elastic portions and are suitably joined together, such as by ultrasonic bonding, to form a side seam 20. Upon the construction of side seams 20, a waist opening 22 and leg openings 24 are formed. The side seams 20 may be constructed to be manually tearable in order to allow training pant 10 to be disassembled manually by the caregiver, so that it can be easily removed from the child after a bowel movement. A more detailed description of the construction and design of the above-described training pant 10 can be found in U.S. Pat. No. 4,940,464, the contents of which are incorporated by reference herein. One specific manner of supplying elastic side panels 18 is described in U.S. Pat. Nos. 5,224,405 and in 5,104,116, both of which are incorporated by reference herein. The provision of side seams 20 can be accomplished in the manner described in U.S. Pat. No. 5,046,272 which is incorporated by reference herein.

Training pant 10 further comprises a front waist elastic 26, suitably joined to front panel 12, a back waist elastic 28 suitably joined to back panel 14, leg elastics 30 suitably positioned in crotch panel 16, and an absorbent pad positioned between a liquid impermeable outer cover or backsheet 34 and a liquid permeable liner or topsheet 36. A graphic 38 is selectively positioned on front panel 12, and as illustrated comprises a design of a simulated "fly opening" 40, typical of a male's underwear, along with a rainbow, sun, clouds, and cars. The graphic 38 can be any type of desired pattern, artistic feature, or the like, and is desired to be positioned in the article at a selected location.

FIG. 2 illustrates another training pant 42 that can be typically used for young girls. This training pant 40 includes a graphic 44 representative of the different types of appearance-related components that can be included in a disposable absorbent article. The graphic 44 includes simulated waist ruffles 46, simulated leg ruffles 48, along with a rainbow, sun, clouds, wagon, and balloon. Again, any suitable graphic can be utilized so as to convey an aesthetically and/or functionally pleasing appearance to the user and caregiver.

Figure 3:
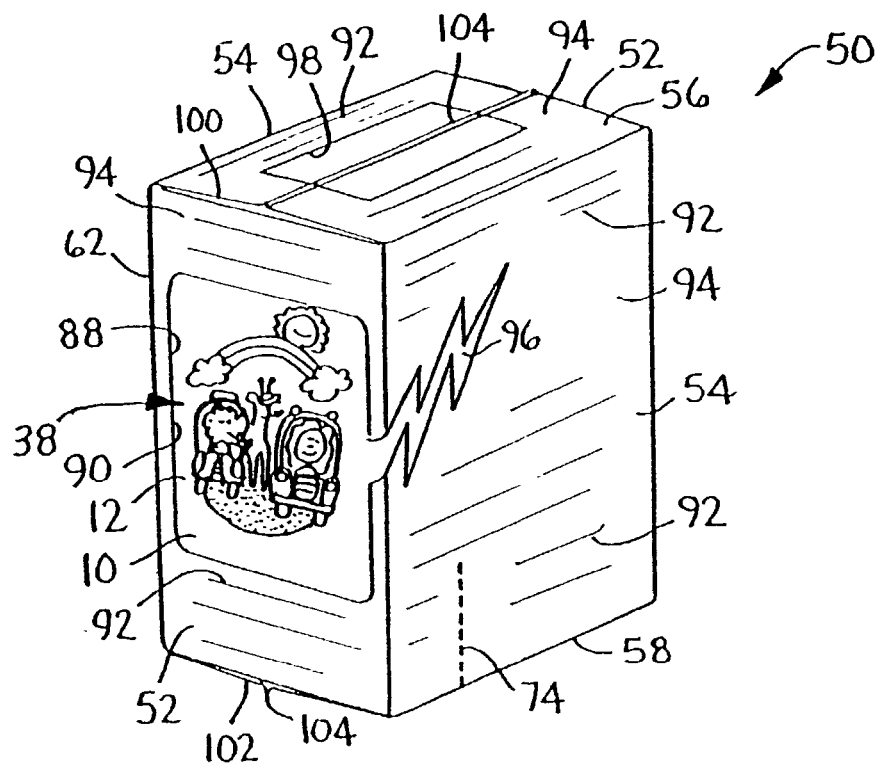
FIG. 3 illustrates a perspective view of one bag of the present invention.
Figure 4:
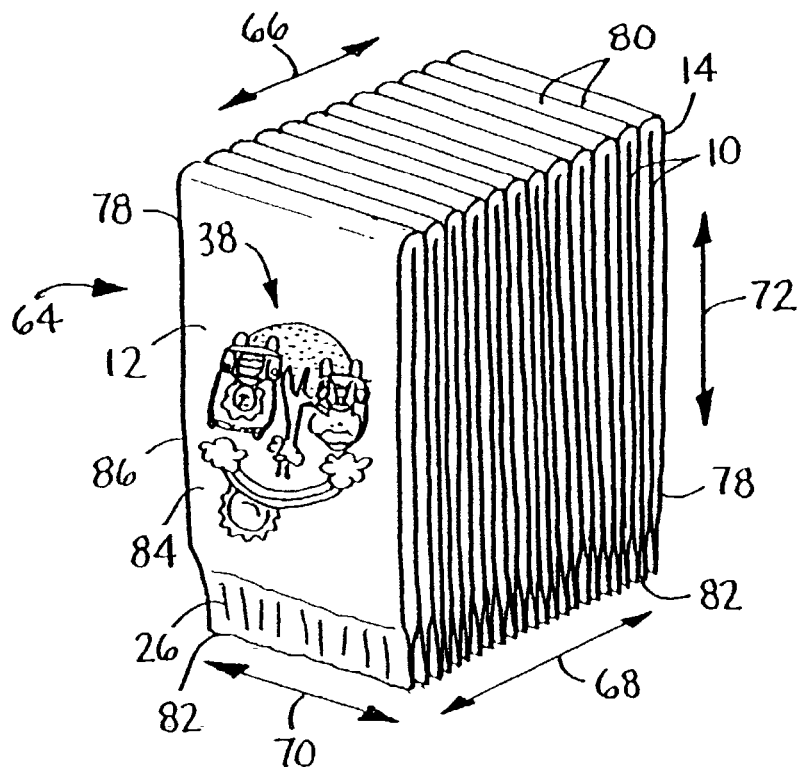
FIG. 4 illustrates a perspective view of a stack of articles.

Referring primarily to FIG. 3, there is illustrated a flexible packaging bag 50 having a polyhedral shape defining or forming a polyhedral enclosure. Specifically, bag 50 has a hexahedral shape that forms or defines a hexahedral enclosure. Bag 50 is defined by a pair of end walls 52, a pair of side walls 54, a top wall 56, and a bottom wall 58. Each of the walls has a periphery, such as periphery 62 for an end wall 52. The walls 52, 54, 56, 58 define an interior space 60 (FIG. 10) for containing a compressed stack 64 (FIG. 4) of articles, such as training pants 10. The term "compressed articles" or similar terminology will mean that the stack of articles, such as training pants 10 in FIG. 4, are compressed inwardly by a compression force at their front and back surfaces or panels, such as front panel 12 and back panel 14, in a direction parallel to stack direction 66 (FIG. 4), so as to decrease the length dimension 68 of the originally, uncompressed articles. The compressed stack 64 also includes a width dimension 70 and a height dimension 72. The term "compression packed" or similar terminology describes the state or condition of training pants 10 after they have been compressed and inserted into bag 50. The term "expansion force" or similar terminology refers to that generally equal force exerted by the compressed stack 64 in a direction generally opposite and parallel to the compression force and against primarily end walls 52. Naturally, all of the walls of bag 50 experience some degree of tension.

Bag 50 may be composed of different materials, or may be composed of substantially the same type of materials. Typically, the material is a polymer film which is sufficiently flexible to assume a desired, generally hexahedral shape when bag 50 is substantially filled with training pants 10. In addition, the material should have sufficient strength to hold and contain the training pants 10, or other articles, without breaking and without excessive bulging or stretching of the film material. For example, the film material may be composed of a polyethylene film or film laminate having a thickness of about 2.5 mils (about 0.0635 millimeters). Other examples include a LDPE (low density polyethylene) film, a LDPE/LLDPE (linear low density polyethylene) film laminate, a LDPE/MDPE (medium density polyethylene) film laminate, a LDPE/HDPE (high density polyethylene) film laminate or the like. Naturally, the dimensions of bag 50 will depend upon the types of articles to be contained therein as well as the desired or aesthetically preferred shape. A suitable bag, and its method of construction, is illustrated and described in U.S. Pat. No. 5,282,687, the contents of which are incorporated by reference herein.

Figure 10:
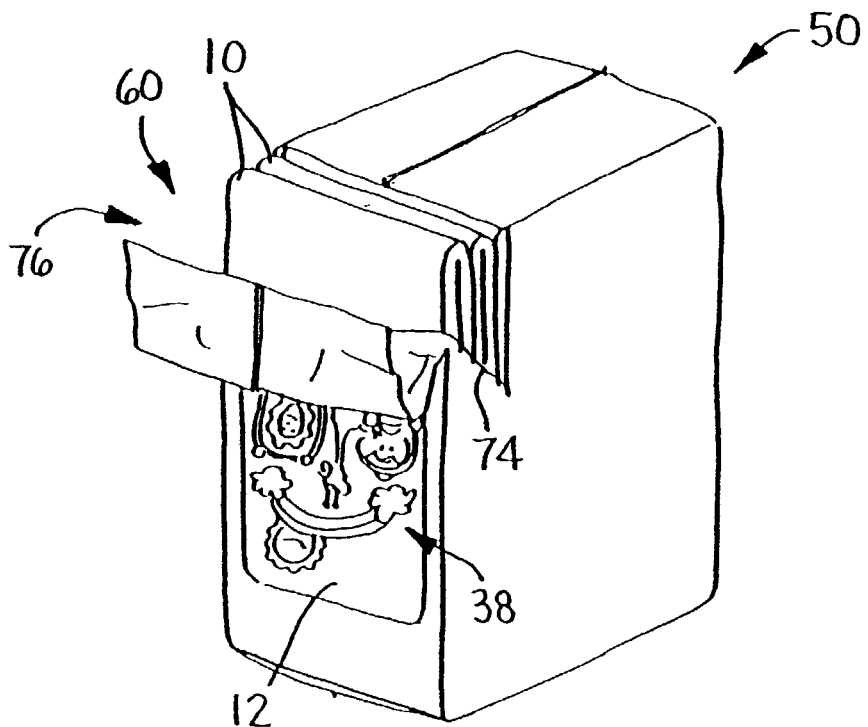
FIG. 10 illustrates a bag that has been opened to expose the interior space and the articles contained therein.

Bag 50 further includes a means, in at least one of the walls, for accessing the interior space 60 (FIG. 10) for dispensing the training pants 10 therefrom. The means for accessing can be a frangible line that is easily broken. A frangible line 74 (FIG. 3) can be disposed or manufactured at any position or location on bag 50 that would permit dispensing training pants 10 therefrom. As illustrated in FIG. 3, frangible line 74 is partially located in one side wall 54, continues underneath along bottom wall 58, and then upwardly along the opposite side wall 54 about the same distance as in the other side wall 54. This is also illustrated in FIG. 10 where frangible line 74 has been torn in order to provide an opening 76 for accessing and dispensing training pants 10. Frangible line 74 may, for example, be provided by partially cutting or otherwise thinning through the thickness of the bag material in a predetermined pattern, providing a selected pattern of perforations along the desired sections or walls of the bag, providing a desired pattern of stress-fatigue weakening along a desired line of the bag, or the like. As illustrated, frangible line 74 is provided by a line of perforations in which there can be approximately 2–10 perforations per lineal inch.

Referring now primarily to FIG. 4, each training pant 10 has been folded such that the elastic side panels 18 (FIG. 1) are inwardly disposed between front panel 12 and back panel 14. As illustrated in FIG. 4, each training pant 10 generally defines opposing side edges 78, a top edge 80, a bottom edge 82, opposing face surfaces 84 (only one of which is illustrated in FIG. 4), and a periphery 86. When the pants are compression packed in bag 50, surfaces 84 face along stack direction 66. Accordingly, the top edges 80 (as viewed in FIG. 4) of training pants 10 contact bottom wall 58, the bottom edges 82 of the training pants 10 contact the top wall 56 of bag 50, the side edges 78 of the training pants 10 contact the bag side walls 54, and the outermost face surface 84 of the end training pants 10 contact end walls 52. Note that the bottom edge 82 of a training pant 10 in FIG. 4 corresponds to the waist opening 22 (FIG. 1).

With reference primarily to FIGS. 3 and 10, bag 50 is opened by breaking frangible line 74 to gain access via opening 76 to training pants 10. Typically, the separation of frangible line 74 is initiated by breaking a portion thereof, and then propagating the break or tear along frangible line 74 through bottom wall 58 and those portions of side walls 54 into which frangible line 74 is manufactured. By thus breaking frangible line 74, the user can insert a finger or thumb through opening 76 in order to gain access to training pants 10. Thereafter, the user can grasp the top of a training pant 10 and pull it out of bag 50, while the remaining training pants 10 are maintained within the confines or interior space 60.

Referring primarily to FIG. 3, bag 50 further includes a window 88 disposed or positioned within a portion of end wall 52. Window 88 includes a window periphery 90 that has a shape that is substantially similar to the periphery of end wall 52. Window 88 at least substantially frames a component of the training pants 10 contained within bag 50. In FIG. 3, the component framed by window 88 is a portion or segment of graphic 38, which is visually perceivable through window 88. Training pant 10 also could have another graphic on back panel 14, and in this case, it may be desirable to have that graphic on back panel 14 visually perceivable through the end wall 52 opposite from the end wall 52 that has window 88 framing graphic 38. In this case, the opposite end wall, i.e., that end wall not visible in FIG. 3, would also have a window.

Depending upon the type of articles to be contained in bag 50, and the components, such as graphics, of those articles, it may be desirable to have a window in a different wall from end walls 52. For example, should a stack of articles be packaged in a different orientation in bag 50, then one of the side walls 54, or the top wall 56 or the bottom wall 58, can have a window to permit a component to be visually perceived therethrough.

In referring to window 88 framing a component, such as graphic 38, the term "framing", "substantially framing", or variations thereof, means that the window periphery surrounds or encompasses all or at least a portion of the component for visual display. Within the context of this description, a component is visually perceivable if it is clear or substantially clear to the person viewing it. The term "clear" refers to the material capability of transmitting light so that the component, or a portion thereof, can be seen as clearly as if there were no intervening material between the component and the individual. The term "substantially clear" refers to the capability of transmitting light, but causing sufficient diffusion of the light to eliminate perception of distinct images, shapes, forms, or the like.

The present invention thus provides the feature of permitting a user, caregiver, or the like, to visually see or perceive a component, or a portion thereof, of the article that they are purchasing, which is particularly desirable when the articles are packaged in a bag. The purchaser also can see or determine the size of the article, thereby providing a degree of confidence in proper fit. This provides product visibility at the time of purchase which is important both to the user and caregiver. For example, when bag 50 contains training pants 10, a child can see the gender-specific graphic, as well as the specific product being selected. This provides the child with a sense of ownership and an active role in the toilet training process. This is extremely important in encouraging the child to become toilet trained. Equally important is that the caregiver can see a desirable feature or component of the product. For example, if a training pant 10 has a unique outer cover that is, for example, both cloth-like in texture and includes a unique design or graphic, then the caregiver can have a high degree of confidence in the product being selected for purchase.

In manufacturing packaging bags, such as bag 50, for containing and dispensing articles, such as training pants 10, it is customary to print the bag material, either on its outermost surface or its innermost surface, with a color, illustrations, written instructions, source of manufacture, or the like. In this description, the term "background" or variations thereof will refer to the surrounding, primarily discernible or perceivable color or ink image printed on the bag 50. For example, if training pants 10 are manufactured as gender-specific pants, such as training pant 10 in FIG. 1 and training pant 42 in FIG. 2, then bag 50 can have a background color of blue for boys, and pink for girls. In this case, the surrounding, primarily perceivable or discernible color would be the blue or pink. The term "copy" will refer to written indicia, numbers, letters, symbols, artistic images or patterns, or the like. Generally, copy is either printed over the background, or over areas of the bag 50 not printed with background. In the example above of a background being a blue color for boys, the blue colored bag 50 could have a printed illustration of the training pant, along with other illustrations and written instructions for proper use. Similarly, a pink colored bag 50 could have an illustration of the girl's training pant, as well as instructions on proper use. The term "substantially transparent" refers to that portion of bag 50, or all of bag 50, that is free of background, but which may have copy. An example of this would be one of the walls of bag 50 being free of background, but including printed written instructions for use.

Referring primarily to FIG. 3, bag 50 includes copy 92 illustrated as generally horizontal lines. That portion of bag 50 outside of copy 92 can have a background, such as a printed blue or pink color earlier described. Consequently, in viewing end wall 52 having window 88, an individual would visually see a background 94, for example a blue or pink color; copy 92, which could be written instructions or other data; and window 88 through which graphic 38 can be visually perceived.

In some instances of arranging bags 50 on a shelf for retail purposes, it may not be practical to orient the bags 50 so that windows 88 are visible. In this instance, for example, bags 50 might be oriented on the shelf space such that one of the side walls 54 is visible. In order to draw attention to end wall 52 having window 88 with graphic 38 viewable therethrough, a visual cue 96 is disposed or arranged in at least one of the side walls 54. Visual cue 96 is at least substantially clear, and as illustrated in FIG. 3, has the shape of, by way of example, a lightening bolt. It should be noted that for purposes of explanation and clarity, visual cue 96 does not show the side edges 78 (FIG. 4) of the individual training pants 10 contained therein. Once a viewer sees visual cue 96, his or her attention will be drawn to the end wall 52, so that a component, such as a graphic 38, of an article, such as a training pant 10, can be visually perceived. Visual cue 96 also can serve as a product-remaining indicator or gauge, so that a caregiver can easily determine the number of pants 10 remaining in bag 50.

Visual cue 96 may or may not be continuous with window 88. In other words, as illustrated in FIG. 3, visual cue 96 and window 88 form a closed loop pattern or periphery. However, it may be desirable for manufacturing, printing, or packaging purposes to have visual cue 96 and window 88 provided as separate areas of visibility. In the latter case, visual cue 96 still serves to draw the attention to window 88 and graphic 38. Thus, visual cue 96 is visually associated with window 88 to draw attention of the purchaser, user, or the like, to window 88 and graphic 38.

Continuing to refer primarily to FIG. 3, bag 50 further includes an accessory window 98 in top wall 56. Due to the particular construction of bag 50, top wall 56 includes a top gusset 100, while bottom wall 58 includes a bottom gusset 102. This particular construction is described in greater detail in the aforementioned, incorporated U.S. Pat. No. 5,282,687. Irrespective of whether top wall 56 has a top gusset 100 or not, accessory window 98 permits at least a portion of the contents therein, such as training pants 10, to be visually perceived. Accessory window 98 can be positioned or manufactured in any of the walls of bag 50, but it is desired that it is in top wall 56, so that the user can determine the number of training pants 10 remaining in bag 50. It will be noticed that there is a seal 104 in top wall 56 which is associated with the manufacturing of top gusset 100, as well as a similar seal in bottom gusset 102. Accessory window 98 is not required to be in the particular wall having a gusset. As with window 88, accessory window 98 can be either clear or substantially clear, and may include copy as long as that does not interfere with the desired purpose of accessory window 98. If desired, accessory window 98 can also be used to draw the attention of the purchaser, user, or the like, to window 88 and graphic 38. Accessory window 98 can take any shape, design, or form that is aesthetically pleasing and/or that provides a means to draw attention to window 88. FIG. 9 illustrates accessory window 98 in top wall 56, while FIG. 8 illustrates a modification thereto in which accessory window 98 extends to the extremities or ends of top wall 56 that are adjacent or contiguous with end walls 52.

Figure 5:
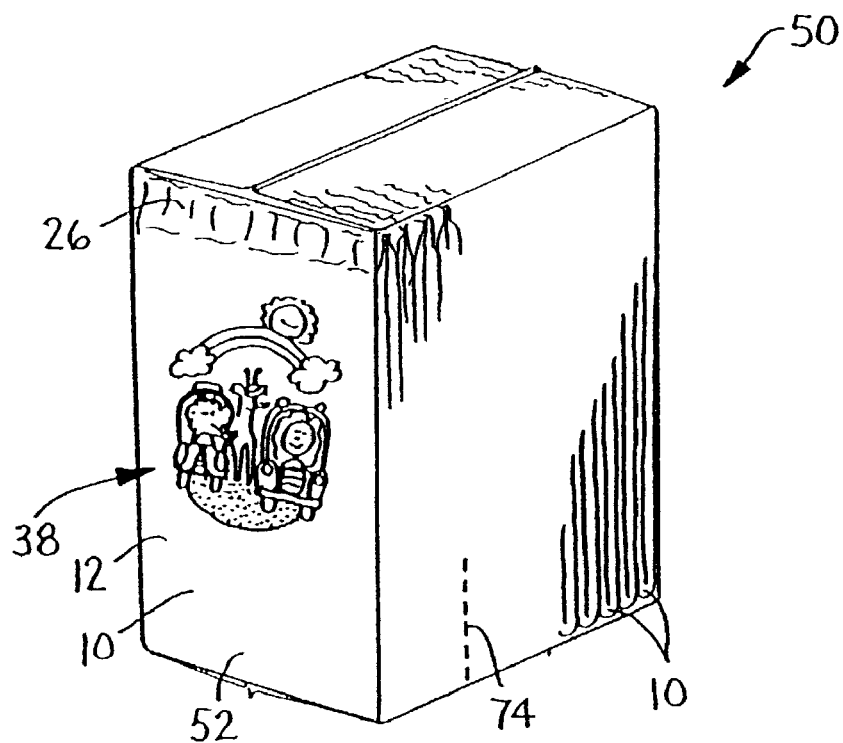
FIG. 5 illustrates a perspective view of a second bag of the present invention.

The present invention contemplates various features as represented in the drawings. In FIG. 5, all of bag 50 is made of a clear, or substantially clear, material, so that most, if not all, of the individual training pants 10 can be visible. However, it may be necessary to include some copy material, and to that extent, most of training pants 10 will be visible.

Figure 6:
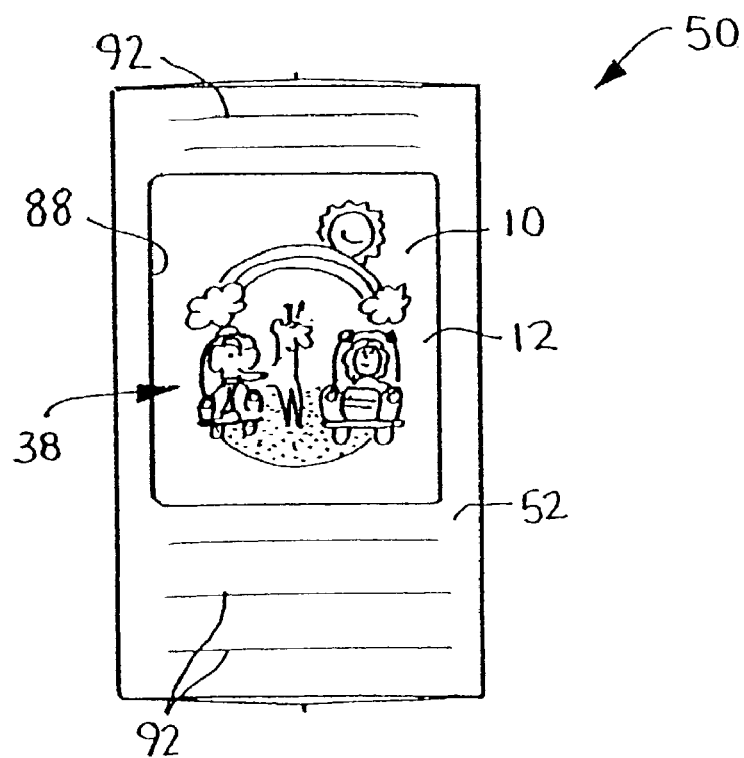
FIG. 6 illustrates a front view of a third bag of the present invention.

FIG. 6 illustrates a bag 50 in which window 88 is positioned completely within the periphery of end wall 52. Copy material 92 is illustrated, but may be eliminated if desired. Again, window 88 may be clear or substantially clear.

FIG. 7 illustrates another variation in which end wall 52 is completely clear, or substantially clear, so that all of the front portion of training pant 10 is illustrated, such as front waist elastic 26 and at least a portion of graphic 38.

Figure 11:
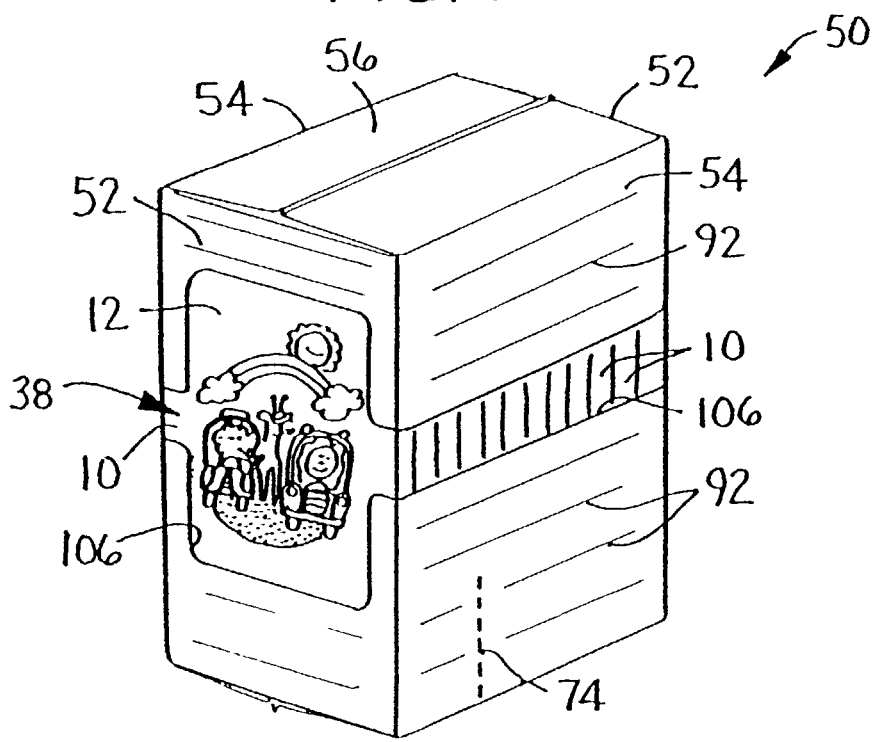
FIG. 11 illustrates a perspective view of a seventh bag of the present invention.
Figure 12:
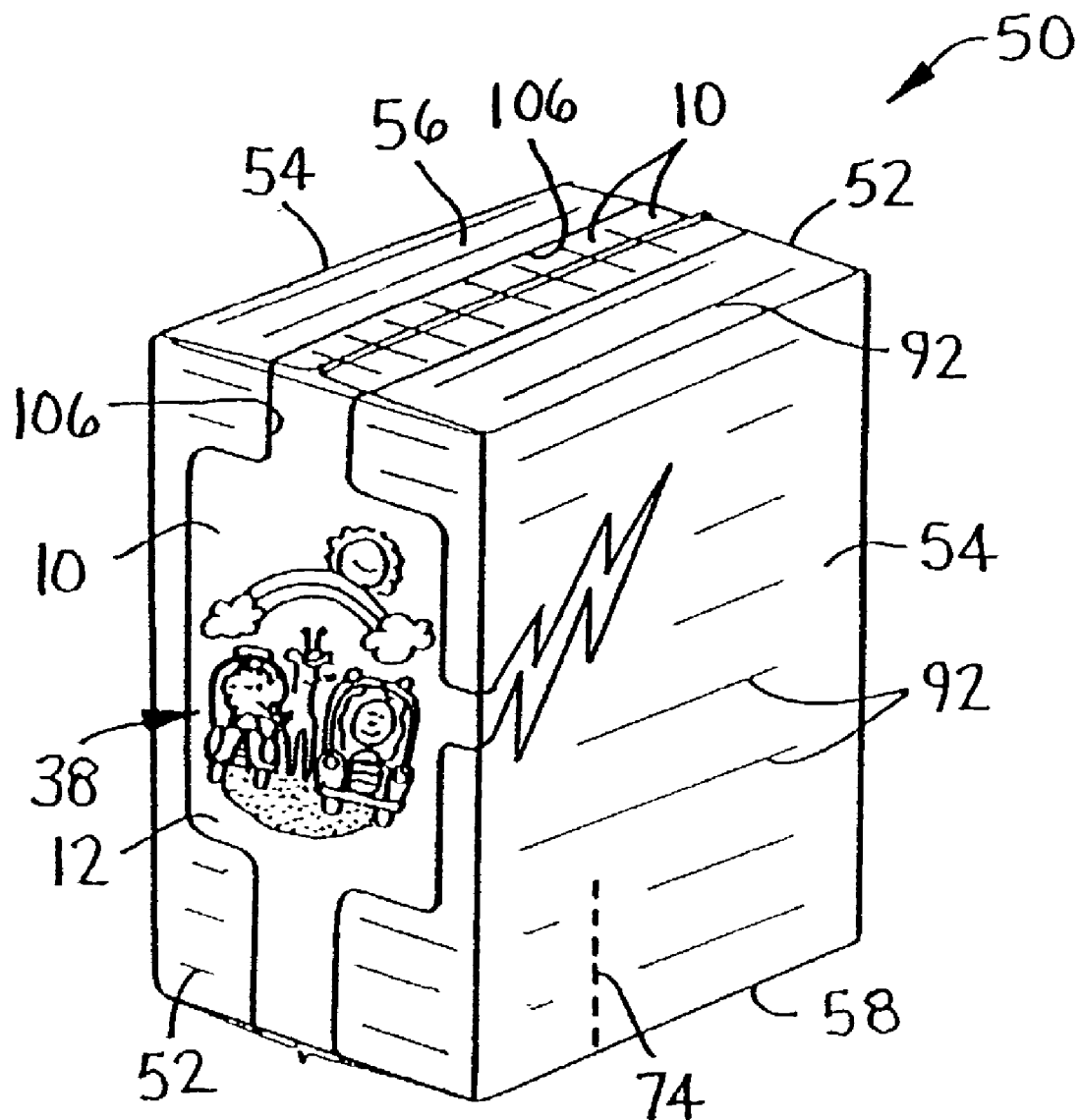
FIG. 12 illustrates an eighth bag of the present invention.

FIGS. 11 and 12 illustrate a wraparound window 106 in bag 50. In FIG. 11, window 106 substantially wraps around four walls of bag 50, specifically end walls 52 and side walls 54. The term "substantially wraps around" means that window 106 may not be continuous around bag 50 due to manufacturing or sealing requirements. However, it is desired that window 106 should continuously wrap around bag 50. The wraparound window 106 also serves to identify the remaining training pants 10 in bag 50. In FIG. 12, window 106 substantially wraps around end walls 52, top wall 56, and bottom wall 58.

While this invention has been described as having a preferred embodiment, it will be understood that it is capable of further modifications. It is therefore intended to cover any variations, equivalents, uses, or adaptations of the invention following the general principles thereof, and including such departures from the present disclosure as come or may come within known or customary practice in the art to which this invention pertains and falls within the limits of the appended claims.

What is claimed:

1. A packaging bag for containing a plurality of disposable absorbent articles, the packaging bag comprising:
    a generally polyhedral enclosure having an interior space, said polyhedral enclosure including a pair of side walls, a pair of end walls, a top wall, and a bottom wall;
    a plurality of disposable absorbent articles contained in said interior space, each one of said articles adapted to be worn by a user and including a front panel and a back panel;
    a first graphic on said front panel of each said absorbent article;
    a second graphic on said back panel of each said absorbent article;
    wherein a first and a second of said walls each include an at least substantially clear portion, said plurality of disposable absorbent articles being folded and positioned in said enclosure such that at least a portion of said first graphic is visually perceivable through said first of said walls and at least a portion of said second graphic is visually perceivable through said second of said walls, and further comprising a window in another of said walls adapted to allow a viewer to determine the number of absorbent articles in the bag, wherein said window substantially wraps around said enclosure.

2. The packaging bag of claim 1 wherein said at least substantially clear portions are each configured as a clear portion.

3. A packaging bag for containing a plurality of disposable absorbent articles, the packaging bag comprising:
    an enclosure defining an interior space;
    a plurality of disposable absorbent articles contained in said interior space, each one of said articles adapted to be worn by a user and including a front panel and a back panel;
    a first graphic on said front panel of each said absorbent article;
    a second graphic on said back panel of each said absorbent article; and
    wherein said enclosure includes at least one at least substantially clear portion, said plurality of disposable absorbent articles being folded and positioned in said enclosure such that at least a portion of said first and second graphics are visually perceivable through said at least one at least substantially clear portion of said enclosure, wherein said enclosure comprises a pair of side walls, a pair of end walls, a top wall and a bottom wall, wherein said at least one at least substantially clear portion is formed in at least a first and second of said walls, and further comprising a window in another of said walls adapted to allow a viewer to determine the number of absorbent articles in the bag wherein said window substantially wraps around said enclosure.

4. The packaging bag of claim 3 wherein said at least one at least substantially clear portion is configured as at least one clear portion.

5. A packaging bag for containing a plurality of disposable absorbent articles, the packaging bag comprising:
- a generally polyhedral enclosure having an interior space, said polyhedral enclosure including a pair of side walls, a pair of end walls, a top wall, and a bottom wall;
- a plurality of disposable absorbent articles contained in said interior space, each one of said articles adapted to be worn by a user and including a front panel and a back panel;
- a first graphic on said front panel of each said absorbent article; and
- a second graphic on said back panel of each said absorbent article; wherein a first and a second of said walls each include an at least substantially clear portion, said plurality of disposable absorbent articles being folded and positioned in said enclosure such that at least a portion of said first graphic is visually perceivable through said first of said walls and at least a portion of said second graphic is visually perceivable through said second of said walls, wherein said side walls, said end walls, said top wall and said bottom wall are each formed at least in part from a flexible material, and wherein said first and second walls each include an opaque portion, said at least substantially clear portions and said opaque portions being integrally formed in said first and second of said walls respectively from the same flexible material.

6. The packaging bag of claim 5, further comprising a window in another of said walls adapted to allow a viewer to determine the number of absorbent articles in the bag.

7. The packaging bag of claim 6, wherein said window is continuous with at least one of said at least substantially clear portion.

8. The packaging bag of claim 5, wherein one of said walls having said at least substantially clear portion further comprises copy.

9. The packaging bag of claim 5, further comprising an access portion on at least one of said walls adapted to allow access to said interior space.

10. The packaging bag of claim 5, wherein said access portion comprises a frangible line.

11. The packaging bag of claim 5 wherein said at least substantially clear portions each comprise a window formed in said first and second of said walls and wherein said opaque portions each comprise a background defining a periphery of each of said windows.

12. The packaging bag of claim 5 wherein said at least substantially clear portions are each configured as a clear portion.

13. A packaging bag for containing a plurality of disposable absorbent articles, the packaging bag comprising:
- an enclosure defining an interior space;
- a plurality of disposable absorbent articles contained in said interior space, each one of said articles adapted to be worn by a user and including a front panel and a back panel;
- a first graphic on said front panel of each said absorbent article;
- a second graphic on said back panel of each said absorbent article; and wherein said enclosure includes at least one at least substantially clear portion, said plurality of disposable absorbent articles being folded and positioned in said enclosure such that at least a portion of said first and second graphics are visually perceivable through said at least one at least substantially clear portion of said enclosure, wherein said enclosure is formed at least in part from a flexible material and includes at least one opaque portion integrally formed with said at least one at least substantially clear portion from said flexible material.

14. The packaging bag of claim 13, wherein said enclosure comprises a pair of side walls, a pair of end walls, a top wall and a bottom wall, wherein said at least one at least substantially clear portion is formed in at least a first and second of said walls.

15. The packaging bag of claim 14, further comprising a window in another of said walls adapted to allow a viewer to determine the number of absorbent articles in the bag.

16. The packaging bag of claim 15, wherein said window is continuous with said at least one at least substantially clear portion.

17. The packaging bag of claim 14, wherein one of said walls having said at least substantially clear portion further comprises copy.

18. The packaging bag of claim 14, further comprising an access portion on at least one of said walls adapted to allow access to said interior space.

19. The packaging bag of claim 18, wherein said access portion comprises a frangible line.

20. The packaging bag of claim 13 wherein said at least one at least substantially clear portion comprises a window, and wherein said at least one opaque portion comprises a background defining a periphery of said window.

21. The packaging bag of claim 13 wherein said at least one at least substantially clear portion is configured as at least one clear portion.

22. The packaging bag of claim 14 wherein said at least one at least substantially clear portion comprises first and second at least substantially clear portions formed in said first and second walls respectively.

23. A packaging bag for containing a plurality of disposable absorbent articles, the packaging bag comprising:
- a generally polyhedral enclosure having an interior space, said polyhedral enclosure including a pair of side walls, a pair of end walls, a top wall, and a bottom wall, each of said end walls including an at least substantially clear window having a periphery;
- a plurality of disposable absorbent articles contained in said interior space, each one of said articles adapted to be worn by a user and including a front panel and a back panel;
- a first graphic on said front panel of each said absorbent article; and
- a second graphic on said back panel of each said absorbent article; wherein said plurality of disposable absorbent articles are folded and positioned in said enclosure such that each said periphery of each said window substantially frames at least a portion of one of said first and second graphics, wherein each of said end walls are each formed at least in part from a flexible material, and wherein said end walls each include an opaque portion defining said periphery, said at least substantially clear windows and said opaque portions being integrally formed in each of said end walls from the same flexible material.

24. The packaging bag of claim 23, wherein one of said end walls further comprises copy.

25. The packaging bag of claim 23, further comprising an access portion on at least one of said walls adapted to allow access to said interior space.

26. The packaging bag of claim 25, wherein said access portion comprises a frangible line.

27. The packaging bag of claim 23 wherein said at least substantially clear windows are each configured as a clear window.

* * * * *